(12) United States Patent
Saitoh

(10) Patent No.: US 6,228,153 B1
(45) Date of Patent: May 8, 2001

(54) SOLVENT DELIVERY PUMP ASSEMBLY

(75) Inventor: Toshinori Saitoh, Tokyo (JP)

(73) Assignees: Micro Electronics Inc.; Moleh Company, Ltd., both of Tokyo (JP)

( * ) Notice: Subject to any disclaimer, the term of this patent is extended or adjusted under 35 U.S.C. 154(b) by 0 days.

(21) Appl. No.: 09/354,954

(22) Filed: Jul. 16, 1999

(30) Foreign Application Priority Data

Jul. 21, 1998 (JP) .................................................. 10-205601

(51) Int. Cl.[7] .................................................. B01D 19/00
(52) U.S. Cl. .......................... 96/218; 210/180; 210/198.2; 417/244; 417/313
(58) Field of Search .................................... 210/101, 175, 210/188, 198.2, 416.1, 180; 417/248, 313, 244; 92/79, 80, 151, 152; 96/155, 218

(56) References Cited

U.S. PATENT DOCUMENTS

| | | |
|---|---|---|
| 4,681,678 | * 7/1987 | Leaseburge et al. . |
| 5,053,060 | * 10/1991 | Kopf-Sill et al. . |
| 5,076,769 | * 12/1991 | Shoa . |
| 5,114,314 | * 5/1992 | Fujimoto . |
| 5,290,340 | * 3/1994 | Gatten et al. . |

* cited by examiner

Primary Examiner—W. L. Walker
Assistant Examiner—David Sorkin
(74) Attorney, Agent, or Firm—Lackenbach Siegel

(57) ABSTRACT

A solvent delivery pump assembly for use in high performance liquid chromatography systems, which accurately delivers a solvent (eluent) drawn from a reservoir, and having removed gases, dissolved in the eluent, and then delivering the eluent as desired for analysis. The apparatus comprises two pump units, each with two plungers of different diameters on a single shaft; one of the plungers in one of the pump unit is of a large diameter size for driving a first pump head in large volume, and the other plunger in the other pump unit is of a smaller diameter for driving a second pump head in small volume. In addition, the apparatus further includes a primary pump and a secondary pump; the former being a pair of the first pump heads and the latter being a pair of the second pump heads, respectively; and a heating unit and a phase separator installed between said primary and secondary is pumps with the phase separator installed at the outlet of the heating unit, so as to remove air bubbles in the eluent which is heated by said heating unit before undergoing HPLC analysis.

8 Claims, 8 Drawing Sheets

FIG. 4(a)        FIG. 4(b)        FIG. 4(c)
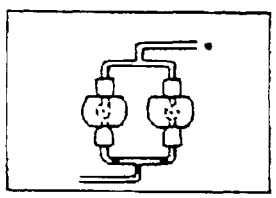  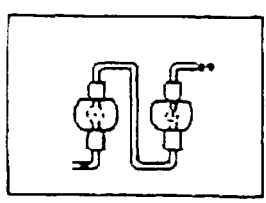  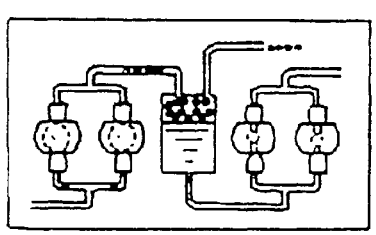
    
FIG. 4(a')       FIG. 4(b')       FIG. 4(c')
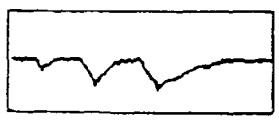  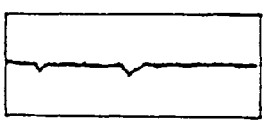  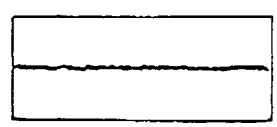

SOLVENT DELIVERY PUMP ASSEMBLY

BACKGROUND OF THE INVENTION

1. Technical Field

This invention relates to a solvent delivery pump assembly which is used for high performance liquid chromatography (hereinafter called HPLC) systems. It removes air bubbles and gaseous components dissolved in eluent (solvent) which is separated and analyzed by the liquid chromatography, thereby allowing to make a fine and precise solvent delivery at a high speed required for HPLC.

2. Background Art

There is a tendency that HPLC used to separate components in a given sample is made more and more highly accurate. Usually in this type of HPLC, an eluent (solvent) drawn from a reservoir by a solvent delivery pump is delivered via a sample injection valve to a detecting section including a separation column. Detected signals are recorded or sent to a monitor screen. In high speed and high accuracy liquid chromatography systems (known as semi-micro HPLC and micro HPLC) which require high accuracy in delivering the eluent under a high pressure yet at a very small quantity, it is common to install such phase separator (gas/liquid separator) as an air trap or a degasser (degassing unit) on the inlet side of the solvent delivery pump in order to insure the stability of the pump.

The purpose of this type of degassing unit is to remove unnecessary gases (air and other gases) dissolved in the eluent. For example, when an electrode reduction reaction is measured, any oxygen dissolved in the eluent greatly influences its measured value. That is, the reduction reaction of the oxygen itself causes a big background current, thereby causing noises to be increased.

FIG. 5 is a block diagram of a system configuration of HPLC. An eluent 2 in a first reservoir 1 is drawn up by a pump 5 through a pipe 3 and degassed by a phase separator 4. It is then delivered through a sample injection valve (auto sampler) 6 and a column 7 to a detector unit 8. The eluent delivered from the detector unit 8 flows out to a second reservoir 10 as a waste eluent 9. The reference arrow marks show the direction of the eluent delivery. Data detected by the detector unit 8 are transferred to a data processing unit 11, wherein they are processed in a visual form or a computer processable data form to provide and store. The column 7 is accommodated in an isothermal oven 7A to prevent the influence of external temperature. The pump 5 and the sample injection valve 6 are controlled by a system controller 12. The phase separator 4 is installed before the pump 5 to insure the stable delivery of the eluent and the accurate analysis by removing gases dissolved in the eluent which is drawn up from the first reservoir 1 by the pump 5.

As the other units and components consisting of this kind of high accuracy liquid chromatography system as well as the function of the whole system are well known so those explanations are omitted.

When the area of eluent delivery rate shifts from the range of 0.01–1.5 ml/min. for conventional HPLC systems to that of 1–300 $\mu$l/min. for semi-micro and micro HPLC systems, the issue of gases dissolved in eluent (so-called air trouble) which is presently a problem is much more serious in order to maintain the accuracy of eluent delivery.

This air trouble is caused by two kinds of air; one is the air contained as bubbles (so-called air bubbles) in the eluent and the other is the one dissolved in it.

Generally, the eluent is reserved in such a container as a reagent bottle (first reservoir 1 as shown in FIG. 5). When it is drawn from the reservoir 1 directly by the pump, the reservoir and the pump are connected by a capillary tube 3 such as PTFE tube. Therefore, the eluent always passes through the capillary tube and is passed into the pump 5. When operating the pump 5, it is first checked whether or not there are air bubbles inside the capillary tube. If air bubbles are observed to be existing, they are removed from the tube by manual operation and then the eluent delivery is started. Even if no air bubble is recognized, problems may occur due to oxygen dissolved in the eluent in such a case that the eluent delivery needs to be stable over a long period of time in the area of the flow rates required for micro HPLC. The reason this may be so is because in the suction process of the eluent delivery pump the inside of the pump is in the state of reduced pressure, causing the dissolved oxygen in the eluent to become air bubbles which make the eluent delivery unstable.

For the above two problems, countermeasures are presently taken as explained in the following (1) and (2).

For air bubbles inside the capillary tube connected to the suction port of the pump, a small air bottle (air trap) is provided in front of the suction port, thereby separating the air bubbles and the liquid (eluent) so that the pump can draw the liquid component only. FIG. 6 is a block diagram to explain a compositional example of the air trap. The eluent 2 in the reservoir 1 is drawn up through the capillary tube 3 by the delivery pump 5 (not shown in FIG. 6). The air trap 4A is installed in the capillary tube 31 before the pump 5. The capillary tube 31 from the reservoir 1 is fed into the upper side of the hermetically sealed air bottle 4A with its end opened, and the other capillary tube 41 connected to the pump 5 is connected to the bottom of the air bottle. If the eluent 2 containing air bubbles is transferred into the air trap 4A, the air component (gas phase) and the liquid component (liquid phase) are separated to stay in the top and in the bottom of the air trap, respectively. The pump 5 draws only the liquid component from its bottom. The air trap 4A is also provided with a capillary tube 32 and a valve 33 in its top to take the separated air component out of it. That means, when the pump 5 draws the eluent inside the air trap 4A, the pressure in it is reduced. As the inside of the reservoir 1 is in the atmospheric pressure, the eluent 2 is sent through the capillary tubes 3 and 31 into the air trap 4A. If air exists in the eluent, the components of air and liquid are separated and stored in the upper and lower portions of the air trap 4A, respectively. Thus, the pump 5 is able to deliver the eluent alone without sucking the air. Air is gradually collected in the air trap 4A as time goes by, which is removed suitably through the capillary tube 32 by opening the valve 33.

For air bubbles existing inside the capillary tube connected to the suction port of the pump, a degassing unit (degasser) is installed prior to the suction port to separate the air component from the liquid (eluent) so that the pump can draw the liquid component only. FIG. 7 is a block diagram to explain one construction example of the degasser. The eluent in the reservoir is drawn through the capillary tube 31 by the pump, and the degasser 4B is installed in the capillary tube 31 prior to the pump 5. The degassing module is composed of a number of tubes made of such gas permeable resin film as PTFE with multi-connectors 16a and 16b connected at their both ends. While the eluent passes through the tubes, gases dissolved in it are extracted to the vacuum chamber 13, thereby avoiding the generation of air bubbles in the eluent delivery pump 5 during its suction process. However, mainly removed by this degasser is dissolved oxygen, and large air bubbles passing through the degasser. It apparently looks that the air trouble can be solved by using the air trap, but practically there are some points of problems that still are a cause for trouble.

The first problem is that it is not feasible to keep good conditions on the operation of HPLC system for continuous use over a long period of time.

When using the air trap, it is required to check an amount of air in the trap, which needs to be removed by manual operation if too much air is included. Under this kind of operational conditions, it is not possible to check all the time the amount of air which is gradually accumulated during the operation for long time, thus making it difficult to run the pump continuously. Consequently, the means of removing air bubbles by using the air trap cannot be adopted under such conditions that an automated instrument with the pump built in is operated continuously for several (ten) days.

The second problem is that the smaller the amount of eluent delivery becomes in the area of micro HPLC, the larger is the possibility of causing the air trap not to work effectively. As the aforementioned PTFE tube, in many cases, is used for the eluent delivery, air penetrates from outside into the inside of the tube through its film when the pump is stopped at night, which causes air bubbles inside the tube of the inlet side. This type of visible air in large amount is removed by the air trap. In the area of micro eluent delivery, however, it becomes a problem as an extremely fine amount of air bubbles is created inside the pump when the eluent is drawn into it. For example, at a delivery rate of several ten $\mu$l/min., even air bubbles of below 1 $\mu$l/min. greatly lose the stability of the eluent delivery. It is considered that small air bubbles created inside the pump are caused by temperatures of the eluent being different between in the air trap and inside the pump.

Usually, the temperature of the air trap is close to the room temperature as the air trap is installed outside the pump.

On the contrary, the temperature inside the pump is higher than a normal room temperature because heat generated by the motor and other electrical units transfers to the pump. The lower the temperature, the larger the degree of gas dissolution in liquid, and therefore, when the liquid in the air trap is drawn into the inside of the pump at higher temperature the degree of gas dissolution reduces. Air bubbles are generated by this difference in temperature. When the pump is in the suction process, its inside is at reduced pressure, which causes more air to be created. The volume of small air bubbles is relatively negligible if the volume of such a pump as a conventional one is large.

However, if the pump becomes small in its volume of 32–8 $\mu$l/min. in the area of micro eluent delivery, even small air bubbles are no longer negligible.

In this connection, if no consideration is made for the change in gas dissolution degree due to the change in liquid temperature in the area of the micro eluent delivery, it is difficult to get the stable eluent delivery over a long period of time.

On the other hand, there are problems to use conventional degassers for the micro eluent delivery as they are made for conventional HPLC.

The biggest problem is that their degassing module is too large in capacity. As explained in FIG. 7, the conventional degasser removes gases dissolved at edge portions of air bubbles by passing the eluent through the inside of the degassing module composed of a number of PTFE tubes which outsides are at reduced pressure.

If the volume of this degassing module is 12 ml and if the pump delivery speed is 1–1.5 ml/min., the degassing module is most suitable in capacity.

However, it is too large if the delivery speed is in the order of 0.3–0.05 ml/min. or 0.05–0.005 ml/min. Thus, to meet the micro eluent delivery requirements, it is essential to make the capacity of degassing module small.

It is possible to make the volume of this type of conventional degassing module simply small by making the length of PTFE tubes (typically 2,500 mm) short. However, it deteriorates the replacement efficiency of the eluent inside the degassing module, resulting in a lower efficiency of degassing.

The reason for this is because as PTFE tubes are made shorter the difference of flow resistance created when the eluent passes in the tubes becomes larger, thereby causing the eluent replacement efficiency to get worse. If this is simply explained, it is because the eluent in PTFE tubes of a small resistance passes in a short time.

Many of those who use solvent delivery pumps seem to think that air bubbles can effectively be removed by using a degasser. But, it is wrong. Probably, the term degasser may give some image that all air troubles can be solved if it is used.

The purpose of the "degasser" is to remove gaseous components dissolved in the eluent, but not to remove air bubbles themselves.

For example, the amount of oxygen dissolved in water is 8–9 ppm in maximum, which can be reduced to more or less 1 ppm by the use of the degasser. Thus, it may be considered that the degasser can reduce approx. 8 ppm in oxygen dissolution. Suppose that the pump is delivering the eluent at a rate of 1 ml/min., the volume of air (oxygen) corresponding to the change of the dissolution, which is removed by the degasser, is 5.6 $\mu$l.

The volume of this, if applied to air bubbles, represents extremely small air bubbles, and large ones that are clearly visible cannot be removed by the degasser.

Even if the capacity of the degasser is increased five times, the aforementioned value becomes 28 $\mu$l/min. With a degasser capacity made $\frac{1}{10}$, it is 2.8 $\mu$l/min. Thus, if air of more than these volumes comes into the degasser, it passes through the degasser.

It is understood from the above explanations that it is difficult to maintain the stable eluent delivery over a long period of time in the area of the micro eluent delivery even if the conventional degasser and the air trap are used simultaneously. Therefore, it is needless to say that a new type of degasser (micro degasser) is required to meet the requirements of the micro eluent delivery.

The new micro degasser has been invented by Mr. Toshinori Saitoh, the inventor of this invention, which initial patent application was filed on Nov. 11, 1997 in Japan, followed by a U.S. patent application with the priority claim filed on Nov. 4, 1998 as Ser. No. 09/186,870, now U.S. Pat. No. 5,980,742, granted Nov. 9, 1999.

The micro degasser is provided with a flat film degassing module in small volume, thereby allowing better efficiency in eluent replacement as well as in degassing than any conventional degassers.

FIG. 8 is a cross sectional view of said micro degasser. In this figure, the degasser 4C is provided with a thin flat space to pass the eluent, which is formed by at least two PTFE film sheets instead of using PTFE tubes which is shown in FIG. 7.

The eluent from a reservoir which is not shown in the figure flow into a degassing module 16' through a capillary tube 31 and a connector 104. While the eluent flows and passes between the PTFE film sheets, the air components dissolved in the eluent are extracted to the inside of a vacuum chamber 13, allowing the eluent with air removed to be delivered by a pump 5 through a connector 105 and a capillary tube 41. Further explanations are not believed necessary as the other components are the same as in FIG. 7.

For details on this type of liquid chromatography and degassing unit, refer to U.S. Pat. No. 5,472,598.

It has been attempted to change the eluent delivery pump system as a means to solve troubles caused by air bubbles. Solvent delivery pumps for conventional HPLC are classified into two systems as shown in FIGS. 9(*a*) and 9(*b*). Those illustrations are to explain the types of conventional delivery pump systems and their relations with air troubles. FIG. 9(*a*) shows a parallel delivery pump system and FIG. 9(*b*) a series delivery pump system, respectively, in which 50A and 50B represent pump plungers.

The parallel delivery pump system in FIG. 9(*a*) is most popular, wherein the two plungers 50A and 50B are connected in parallel. The eluent is drawn respectively into the plungers 50A and 50B, and is then sent out alternately from them to keep the eluent delivery continuously, as shown by the arrow marks.

In the series delivery pump system as shown in FIG. 9(*b*), on the other hand, those two plungers 50A and 50B are connected in series, wherein the eluent is drawn into the first step plunger 50A as shown by the arrow mark. The half amount of the eluent sent out from the plunger 50A is drawn by the next step plunger 50B. While the plunger 50A draws the eluent, the plunger 50B sends it out so that by repeating these operations the eluent can be continuously delivered.

Among the above mentioned two pump systems, air bubbles sucked by the pump are removed more readily in the series delivery system of FIG. 9(*b*) than in the parallel delivery system.

One of the reasons for easier air bubble removal lies in the volume of the plunger. In the series pump system of FIG. 9(*b*) the volume of the plunger 50A used is two times that of the plunger 50B, which is also two times that of the both plungers used in the parallel pump system of FIG. 9(*a*).

The use of such big volume plunger as in the series pump system provides one of the reasons for the series pump system with bigger capability to remove air bubbles than the parallel pump system.

The second reason why the series pump system of FIG. 9(*b*) is better in air bubble removal is in the configuration of the plungers. In this system the two plungers 50A and 50B are configured in series, wherein while the first step plunger 50A sends the eluent out the second step plunger 50B draws it in. Consequently, these operations allow air bubbles to be removed more readily than in the parallel pump system.

As such, it is possible to make air bubbles readily removable by modifying the pump system. However, the eluent delivery rate becomes unstable while air bubbles are existing inside the pump.

Another difference between the pump systems of FIG. 9(*a*) and FIG. 9(*b*) is that the time of the delivery or rate is unstable when air bubbles are present as the pump is shorter in the series system of FIG. 9(*b*) than in the parallel system of FIG. 9(*a*).

In this connection, it does not mean that the air trouble can be thoroughly solved by modifying the conventional pump system, but it should be considered that the air trouble becomes less of a problem in the series pump system than in the parallel pump system and that removing the air bubbles is fundamentally difficult.

SUMMARY OF THE INVENTION

The purpose of this invention is to solve the prevailing problems involved in the conventional technological fields and provide a new solvent delivery pump system for liquid chromatography, which allows the accurate eluent delivery without having any undue influence by the presence air bubbles in the eluent (solvent).

To achieve the above purpose, this invention is characterized by a twin head pump assembly comprising of two twin head pump units each of which is equipped with a single shaft with two different diameters to make two plungers for driving two pump heads. With one single shaft, one plunger is made on its large diameter side to drive one pump head and the other on its small diameter side to drive the other pump head. As there are two shafts provided, there are four pump heads available in total, two of which are driven by the large diameter plungers and the other two by the small diameter plungers. One pair of the pump heads driven by the large diameter plungers comprise a primary pump, and the other pair of the pump heads driven by the small diameter plungers comprise a secondary pump. The primary and secondary pumps are connected in series via a heating unit and a gas/liquid (phase) separator.

A typical system configuration of this invention is described below:

(1) The invention is a solvent delivery pump assembly to be used, for example for high performance liquid chromatography (HPLC) systems, which draws eluent from its reservoir, removes gases dissolved in the eluent, delivers the gas removed eluent via a sample injection valve to a detection means including a separation column, and is installed between the reservoir and an analyzing section. This solvent delivery pump assembly is characterized by having the following configuration.

Two pump units each with two sizes of plungers made on two different diameters of a single shaft. One plunger in one pump unit is made on the large diameter side of the shaft to drive a first pump head in large volume, and the other plunger on the small diameter side of the shaft to drive a second pump head in small volume, respectively.

With reference to the primary pump and a secondary pump, the primary pump is composed of pair of the first pump heads and the secondary pump of a pair of the second pump heads, respectively. Those primary and secondary pumps are connected in series.

A heating unit and a phase separator both of which are installed, as best shown in FIG. 1, in line between the primary and secondary pumps. The phase separator is installed on the outlet of the heating unit and removes air bubbles in the eluent heated by the heating unit. The air removed eluent is drawn up by the secondary pump to deliver into the analyzing section.

The above configuration allows to deliver the eluent accurately and precisely without having any influence from air bubbles in it. Furthermore, by installing the heating unit, gases dissolved in the eluent are forcedly purged, making the amount of gas dissolution in the liquid (collected in the bottom of the phase separator) reduced, thereby allowing to deliver even such solvents with low boiling points as methanol, hexane, etc. stably.

(2) The invention is also characterized in that the volume of the first pump head is larger than that of the second pump head, both of which are driven by the single, shaft. By this construction, excessive eluent collected in the bottom of the phase separator is drawn again into the primary pump. Here, although it is suitable to make a ratio of the volume of the primary pump against that of the secondary pump at approximately 2:1, the effect of this invention can be achieved by making the volume of the primary pump larger than that of the secondary pump.

(3) Further characterized is to provide a cleaning channel between the first and second pump heads to automatically clean sealing materials on their atmospheric pressure side. This cleaning channel, also called a cleaning port, is provided behind the sealing material for the secondary pump. By always flowing the eluent in the channel, eluent leaked from the sealing material is washed away, thereby avoiding troubles of damaging the seals due to accumulated crystallized compounds from the leaked eluent.

It is needless to state that this invention is not limited to the compositions and configurations described in this file, and allows to alter them unless it deviates from the concept of this invention stated throughout the descriptions of this file.

BRIEF DESCRIPTION OF THE DRAWING

FIGS. 4(a), 4(b) and 4(c) as well as FIGS. 4(a'), 4(b') and 4(c') explain the differences in comparison between the pump assembly of this invention and conventional series and parallel pump systems.

DETAILED DESCRIPTION OF PREFERRED EMBODIMENTS

Embodiments of the present invention are now described hereinafter with reference to the drawings.

Figure 1:
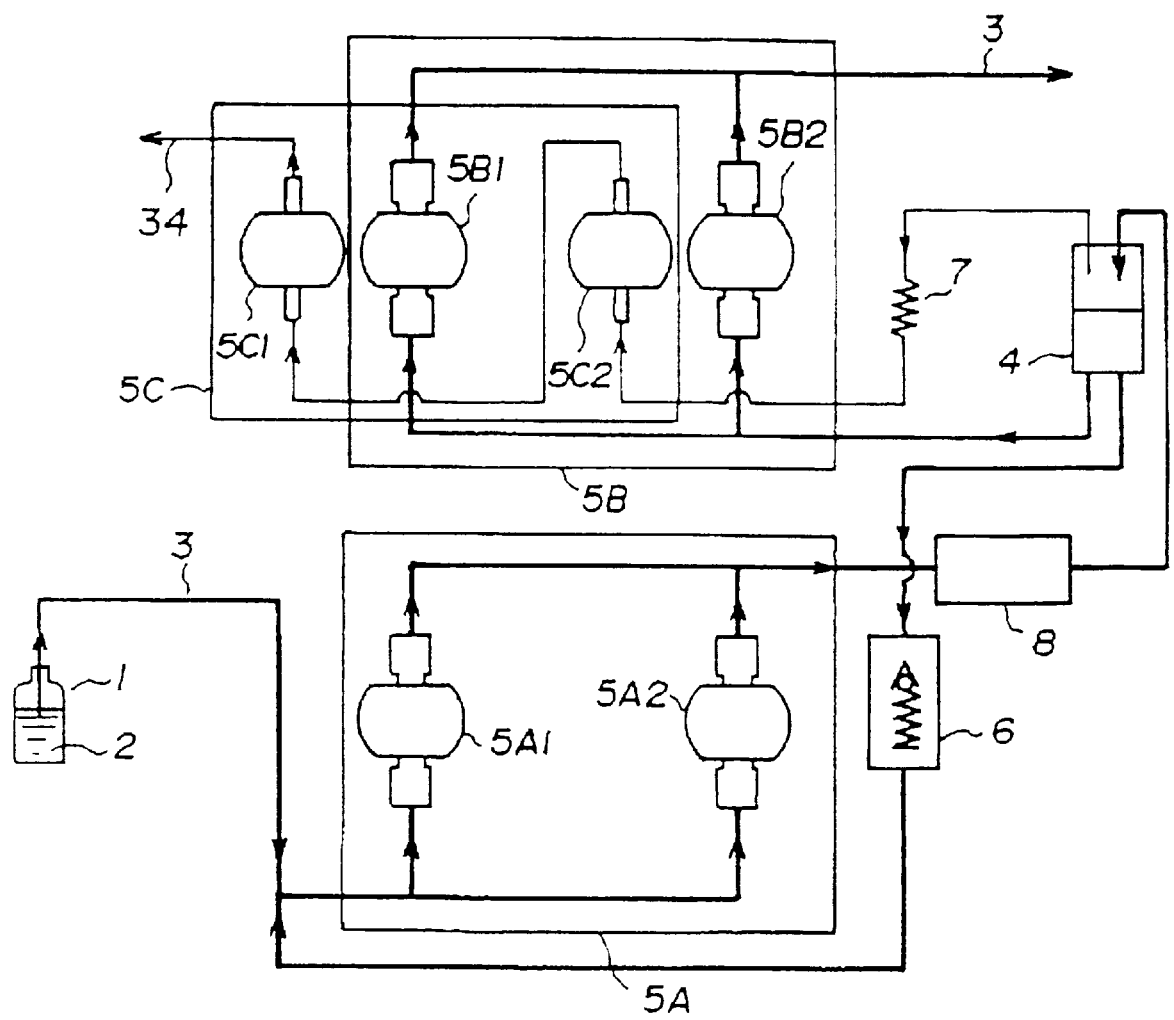
FIG. 1 is a block diagram showing a basic system configuration of the solvent delivery pump assembly, such as one used for for liquid chromatography.

FIG. 1 is a block diagram of a basic system of the solvent delivery pump assembly of this invention for use in typical liquid chromatography systems. In this diagram, shown with respective identification numbers are a reservoir 1, an eluent (solvent) 2, a capillary tube 3, a phase separator 4, a primary pump 5A, a secondary pump 5B, a cleaning channel (cleaning ports) 5C, a first pump head 5A1 for the primary pump, a second pump head 5A2 for the primary pump, a first pump head 5B1 for the secondary pump, a second pump head 5B2 for the secondary pump, a first cleaning port 5C1, a second cleaning port 5C2, a check valve 6, and a liquid separation capillary 7, respectively.

The primary pump 5A and the secondary pump 5B are connected in series, and their flow rates are different to satisfy that a flow rate of the primary pump is larger than that of the secondary pump. For example, the primary pump is set at 200 μl/min. and the secondary pump is set at 100 μl/min., respectively. It is not always limited to those specific values and the ratio if the former is larger than the latter in their respective flow rates.

It is set to make the operational timing of the both pumps all identical. Installed between the primary pump 5A and the secondary pump 5B are a heating unit 8 to heat the eluent and the phase separator 4 to separate air bubbles from the eluent. The eluent delivered from the primary pump 5A is first fed into the heating unit 8 and then to the phase separator 4. As the primary pump 5A is set at a large flow rate, it has enough capacity to discharge the eluent without problems even if a big amount of air bubbles are sucked in.

The eluent containing air bubbles is separated into the air bubbles collected in the top and the liquid component in the bottom of the phase separator 4. The secondary pump 5B draws the liquid collected in the bottom to deliver.

The air bubbles collected in the top of the phase separator 4 and containing a part of the eluent are separated from the liquid by the liquid separation capillary 7 to emit to the outside. The separated liquid (eluent) flows to the cleaning channel composed of the cleaning ports 5C1 and 5C2 which are located between the plungers 5A1 and 5B1 as well as between those of 5A2 and 5B2, respectively so as to clean the back side of the primary pump 5A and the secondary pump 5B. It is then discharged from the drain pipe 34.

As the flow rates are set for the primary pump 5A to be larger than the secondary pump 5B, any excess eluent collected in the bottom of the phase separator 4 is drawn again by the primary pump 5A.

The final accurate eluent delivery is made by the secondary pump 5B, and with this pump system the secondary pump 5B can deliver the eluent without any affection of air bubbles even if much of them is initially contained.

Figure 2:
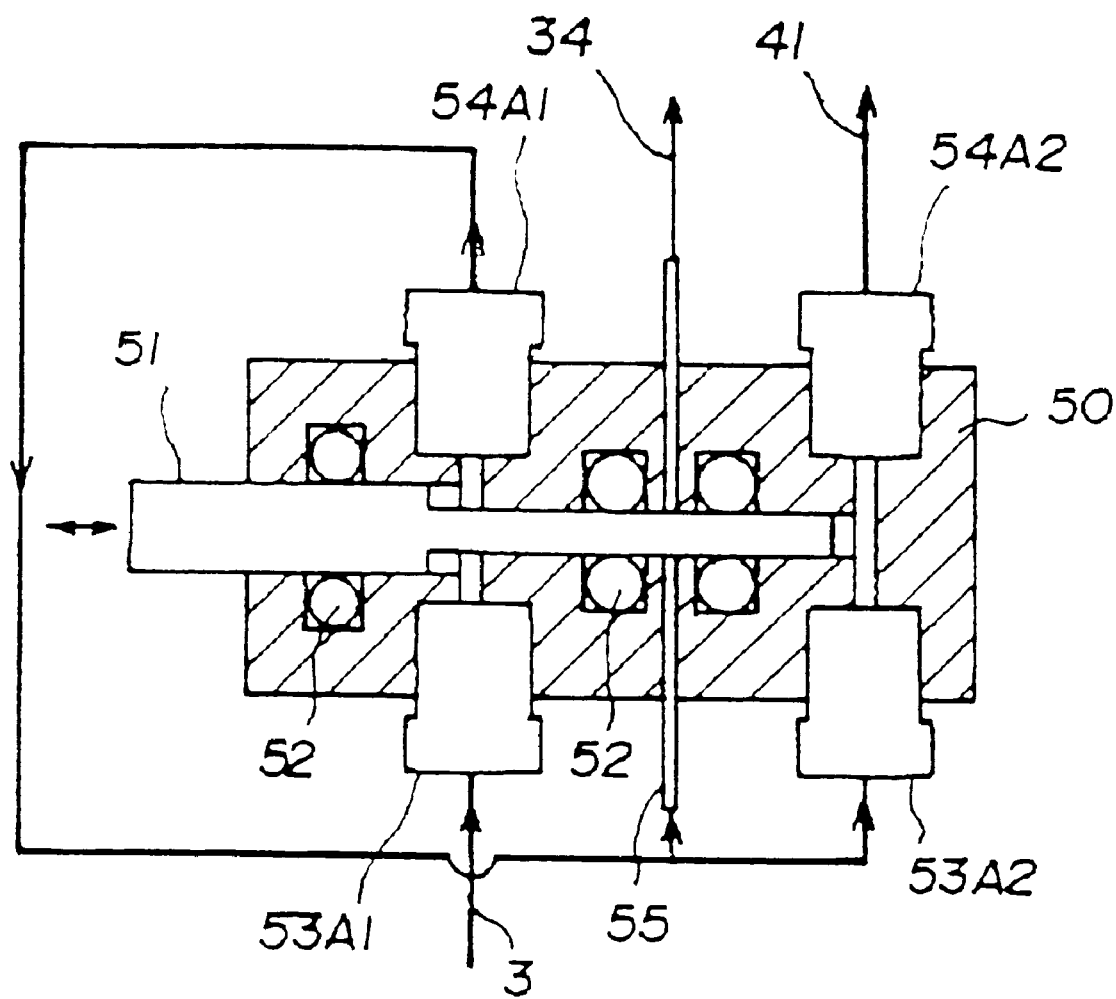
FIG. 2 illustrates typically an example of the pump head unit in one of the pump units shown in FIG. 1.

FIG. 2 shows as an example one of the two pump units comprising the twin pump heads for the primary and secondary pumps. It is composed of two heads operated by a plunger rod 51 made of one single shaft. The plunger rod 51 has two different diameters and forms one plunger on its small diameter side for the secondary pump 5B and the other plunger at the edge of large and small diameters for the primary pump 5A. Also shown are a pump unit 50, seals 52, a suction valve 53A1 for the primary pump, a suction valve 53A2 for the secondary pump, a discharge valve 54A1 for the primary pump, and a discharge valve 54A2 for the secondary pump.

Both pumps are kept independent with the seals 52 in plural number so as not to affect each other. Each of the seals 52 has a part to hermetically seal the plunger for maintaining high pressure inside the pump, the other side of which is exposed to the atmospheric pressure. In the middle of the primary and secondary pumps, the cleaning channel 55 is provided to clean the atmospheric pressure side of the seals for the secondary pump.

With the flow of such liquid as an organic solvent at high pressure in the twin head pump unit 50, even a small amount of the liquid may leak from the seals. As the low pressure side of the seal is usually exposed to the atmospheric pressure, the organic solvent and other liquids with low boiling points are vaporized but dissolved components are crystallized and adhere to the seal. For example, in case a water solution containing salt is delivered to the pump assembly, leaked water from the seal is vaporized but salt is crystallized in powder form and remains to attached to the seal. The salt powder retained on the seal penetrates into the seal itself or moving portion of the seal and pump, making them defective or eroded, which if unchecked can be severe and can cause failure of the pump.

In this embodiment, the cleaning channel is provided for such portions, wherein by flowing of the eluent all the time such pump troubles as mentioned above can be avoided.

Figure 3:
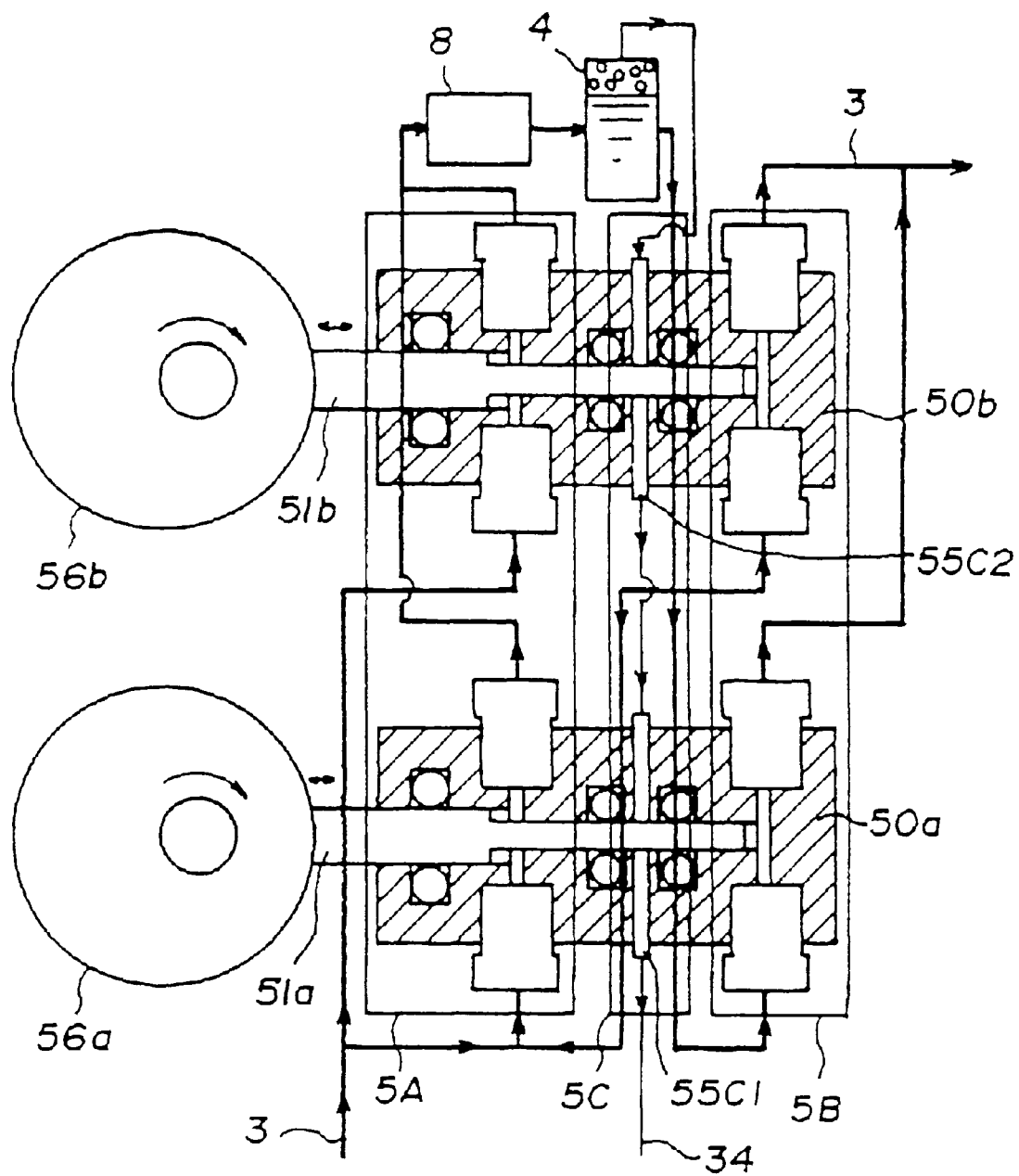
FIG. 3 shows the entire solvent delivery pump assembly of this invention in one of its embodiments.
Figure 5:
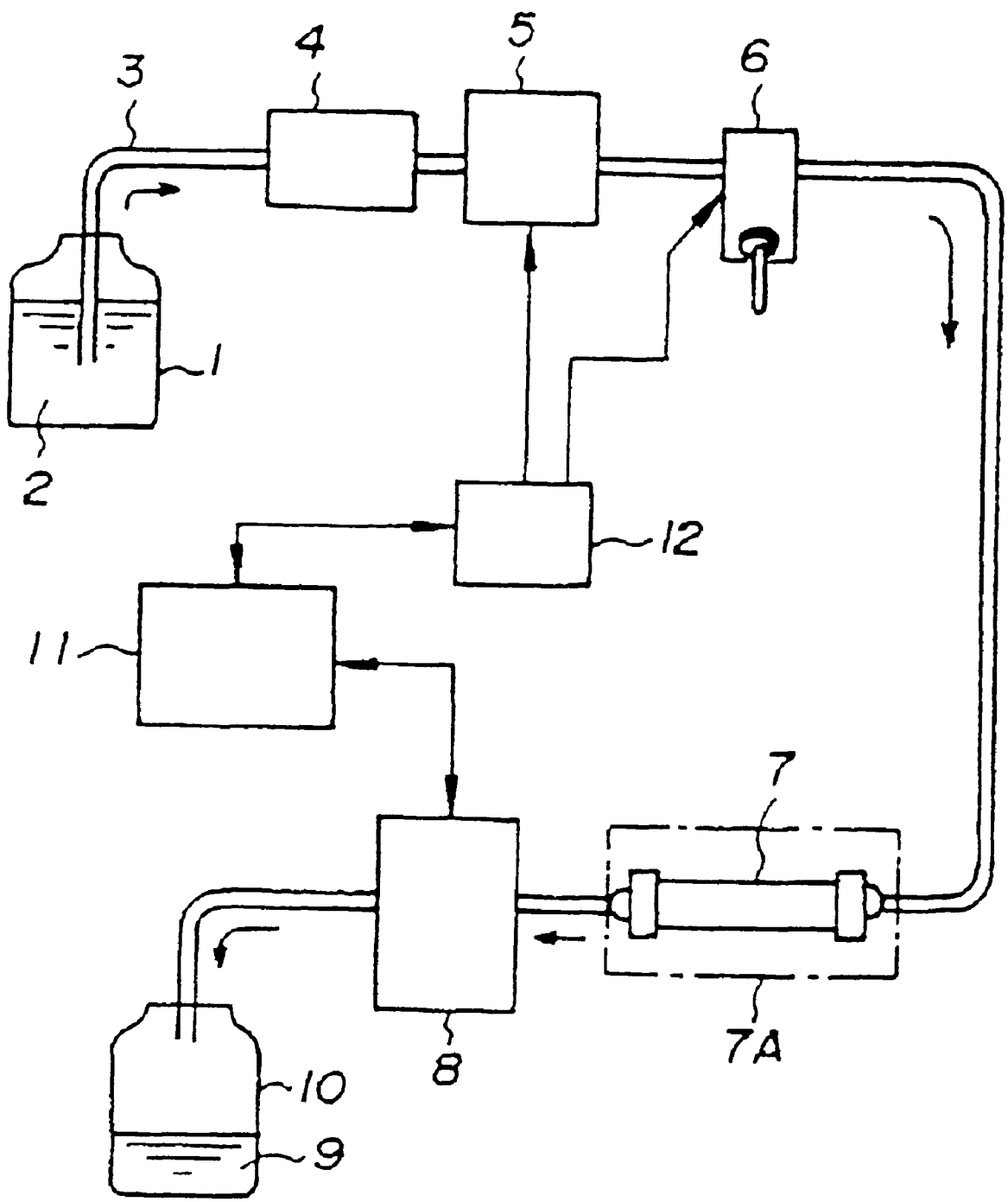
FIG. 5 is a block diagram showing a system and flow configuration in general of an HPLC.
Figure 6:
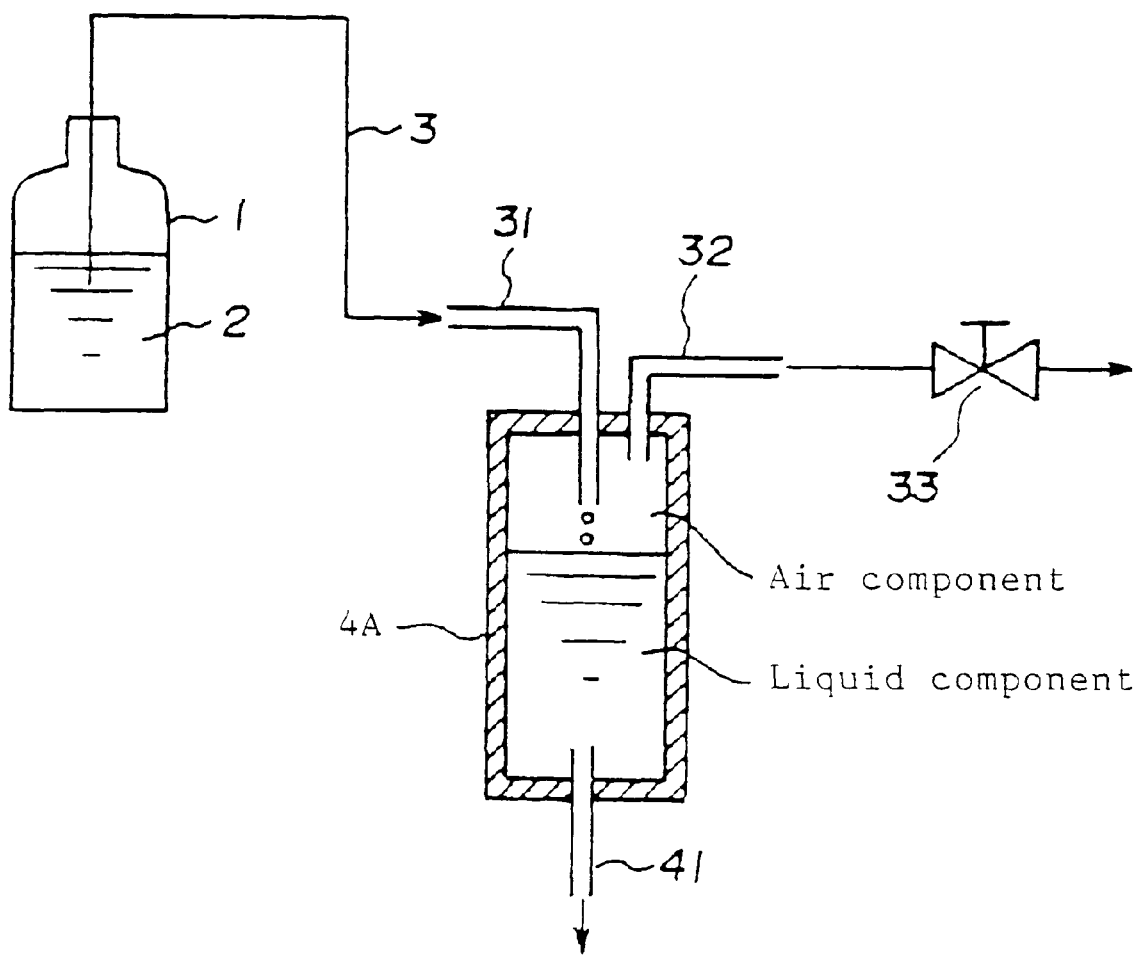
FIG. 6 illustrates an example of an air trap.
Figure 7:
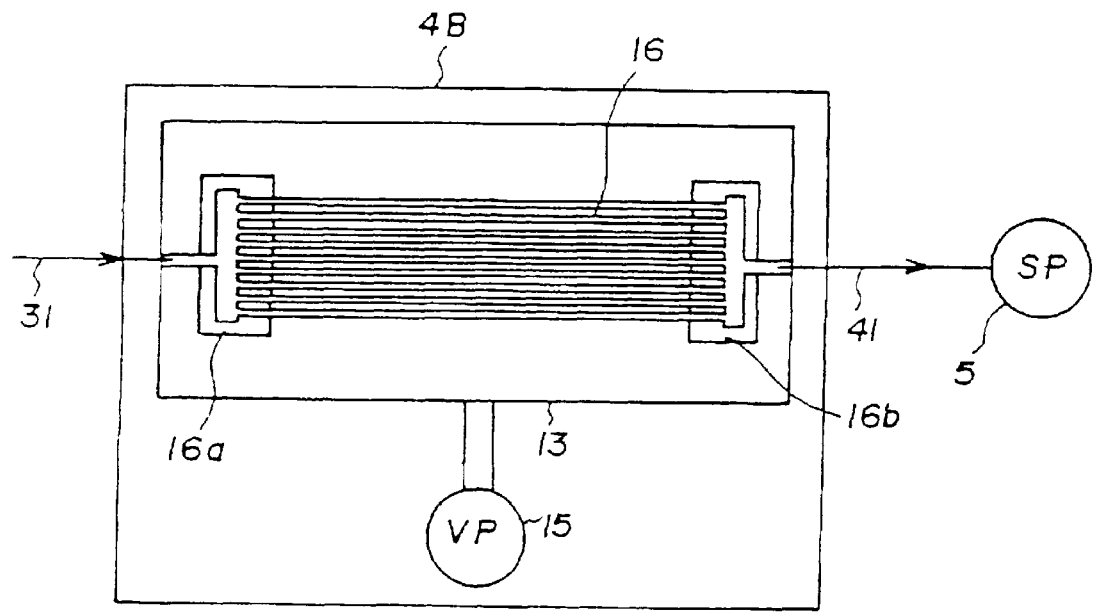
FIG. 7 illustrates and shows a example of a conventional degasser.
Figure 8:
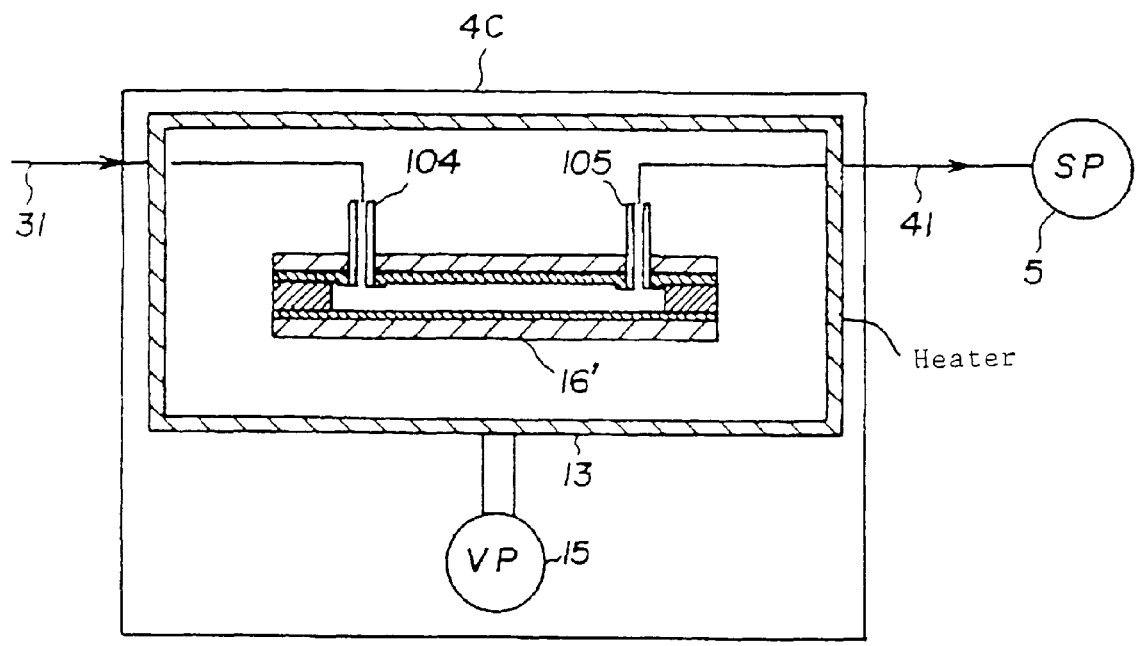
FIG. 8 shows in cross section another construction example of a conventional degasser of the thin film type.
Figure 9A:
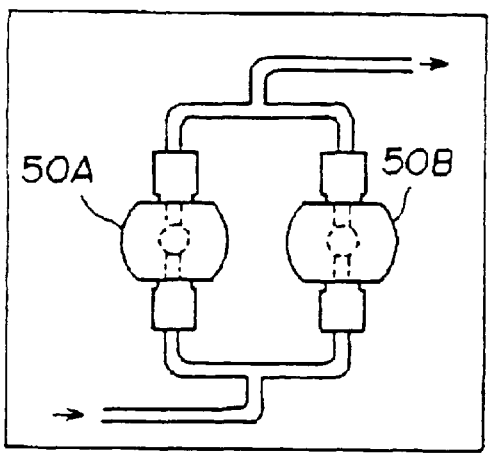
FIGS. 9(a) and 9(b) illustrate conventional solvent delivery pump systems in parallel and in series, respectively.
Figure 9B:
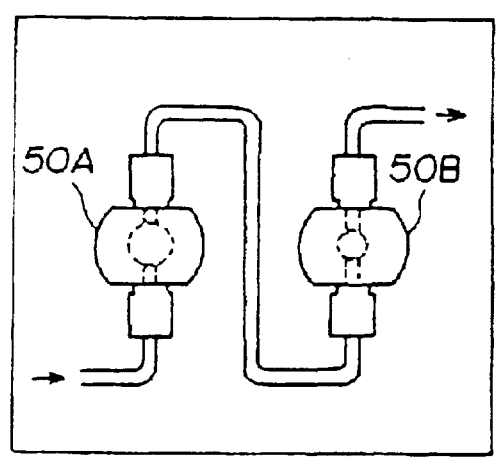

FIG. 3 shows an eluent flow and connections in one of the embodiments for the solvent delivery pump assembly of this invention, in which the two pumps composed of the two twin head pump units as shown in FIG. 2 are connected in series in the way as shown in FIG. 9(b). It may be regarded that in this construction the pump heads 50A and 50B as shown in FIG. 9(b) are replaced with the two pumps in FIG. 3.

In FIG. 3, there is shown twin pump head units 50a and 50b, plunger rods 51a and 51b each of a single shaft with two different diameters, a first cam 56a to drive the first plunger rod 51a and a second cam 56b to drive the second plunger rod 51b. As the compositions of the respective pump heads were explained in FIG. 2, they are omitted here.

The first plunger rod 51a and the second plunger rod 51b equipped in the pump units 50a and 50b, respectively are driven back and forth by the rotation of the cams 56a and 56b. The large diameter sections of the first plunger rod 51a and the second plunger rod 51b comprise the primary pump 5A, and the small diameter sections of the first plunger rod 51a and the second plunger rod 51b comprise the secondary pump 5B.

The eluent containing air bubbles delivered from the primary pump 5A is heated by the heating unit 8, and then is separated into an air component and a liquid component by the phase separator 4. The eluent collected in the bottom of the phase separator 4 is drawn by the secondary pump 5B with a half capacity in eluent delivery of the primary pump and is sent to the analyzing section of the chromatographic instrument.

Air collected in the top of the phase separator 4 is separated from the liquid by the gas/liquid separation capillary 7 and is exhausted outside. The separated eluent floww into the cleaning ports 55C2 and 55C1.

By this embodiment, oxygen dissolved in the eluent is automatically and partially removed and air bubbles are also automatically removed, thereby allowing the secondary pump 5B to make the accurate eluent delivery without any influence of the air bubbles.

Here, it is now explained how to solve the generation of dissolved gases due to a change of temperature inside the solvent delivery pump assembly.

The eluent is first drawn by the primary pump 5A in which air bubbles are initially created as mentioned above. Even if the eluent delivery rate is deteriorated due to the air bubbles created inside the primary pump 5A, if the requirement that the flow rate of the primary pump is larger than that of the secondary pump is fulfilled, the air bubbles will surely pass through the heating unit 8 and is are fed into the phase separator 4. Therefore, the secondary pump 5B allows for the stable delivery of the eluent containing no air bubble from the bottom of the phase separator 4.

One may think that air bubbles can also be created inside the secondary pump 5B as in the primary pump 5A, but no air bubbles are created inside the secondary pump 5B due to the following reasons.

Firstly, gases dissolved in the eluent are substantially removed by generating air bubbles inside the primary pump 5A as well as in the heating unit 8. Then, the gases generated as the air bubbles have already been removed by the phase separator before coming to the suction port of the secondary pump 5B. Also, the temperature condition inside the secondary pump 5B are generally about the same condition as that of the primary pump 5A, thus making air bubbles hardly generated inside the secondary pump 5B.

Secondly, as the capillary tube in which the eluent with air bubbles flows in the capillary tube from the phase separator 4 it exhibits or has a flow resistance to some extent, and the inside of the phase separator 4 is thus in the state of a bit increased pressure. This makes the suction port of the secondary pump 5B in the state of increased pressure against that of the primary pump 5A being at no pressure, providing the condition to hardly create any air bubbles as well.

Furthermore, as the air bubbles have already been generated inside the primary pump 5A, the amount of gases dissolved in the eluent is made smaller and therefore, no more air is created inside the secondary pump 5B.

In this connection, according to the aforementioned embodiment the solvent delivery pump assembly of this invention provides the means to solve the problem of preventing the conventional solvent delivery pump systems from keeping the long term stable eluent delivery due to air bubbles from outside and the generation of those by dissolved oxygen inside the pump, thereby allowing to deliver the eluent in a stable manner precisely over a long period of time.

FIGS. 4a–4c show and compare the solvent delivery pump assembly of this invention and conventional pump systems. FIG. 4(a) shows a parallel delivery pump system as explained in FIG. 9(a), FIG. 4(b) shows a series delivery pump system, and FIG. 4(c) shows a general delivery pump system of this invention as illustrated in one of its embodiments. The pump system in FIG. 4(a) is most popular, in which the eluent is delivered alternately by the two pumps. In the pump system of FIG. 4(b) the first stage pump has a double volume of the second stage pump, which are connected in series. FIGS. 4(a'), 4(b') and 4(c') are graphs of changes in delivery rate to show the immunity of the eluent delivery for air bubbles on the respective pump systems. These graphs are the results of tests made on the accuracy of eluent delivery especially when sucking micro air bubbles.

As clearly shown in the graphs of FIGS. 4(a'), 4(b') and 4(c'), the immunity for micro air bubbles on the pump systems is compared in the order of: (pump assembly of this invention)>(series pump system)>(parallel pump system).

The graphs of FIG. 4(a') and FIG. 4(b') show that air bubbles sucked into the pumps are readily removable in the series pump system of FIG. 4(b) in comparison with the parallel pump system of FIG. 4(a), but in every case of them once they are sucked in, the eluent delivery becomes unstable until they are removed.

On the contrary, as shown in FIG. 4(c'), the stability of the eluent delivery is not affected at all for the pump assembly of this invention even if it draws air bubbles. With the pump assembly shown in FIG. 1 especially by means of the phase separator 4 in the pump assembly of this invention, the air bubbles do not affect performance and it is as if they just pass through the system without any harmful effect.

Consequently, highly accurate analytical operations over a long period of time for liquid chromatography are assured with high reliability by using the solvent delivery pump assembly of this invention.

In addition, the conventional way of cleaning the solvent delivery channels including the inside of the pump systems is made manually as occasion demands or by using a cleaning pump(s) separately installed. In the embodiment of this invention, a cleaning channel is provided so as to clean the atmospheric side of the seals for the secondary pumps. By flowing the eluent from the phase separator into the cleaning channel, the seals are automatically and constantly cleaned, so that even a buffered water solution containing a salt is stably delivered for and over the long run.

What is claimed:

1. A solvent delivery pump assembly which draws eluent from a reservoir, and removes gases dissolved in the eluent, and then delivers the eluent as desired for analysis, comprising:

two pump units, each with two sizes of plungers provided on two different diameters of a single shaft;

one of said plungers in each of said two pump units is of a large diameter size of said single shaft, and drives a first pump head large in volume, and the other of said plungers is of a smaller diameter size of said single shaft, and drives a second pump head small in volume;

said pump units including a primary pump (5A) and a secondary pump (5B), and said primary pump is comprised of a pair of said first pump head, and said secondary pump is comprised of a pair of said second pump head; and a heating unit and a phase separator disposed in line between said primary pump and said secondary pump; with said phase separator installed at an outlet of said heating unit so as to remove air bubbles in said eluent heated by said heating unit.

2. The solvent delivery pump assembly of claim 1, wherein, in each of said pump units, the volume of said first pump head is larger than that of said second pump head, and both of which are driven in common by said single shaft having different diameters; and said single shaft having sealing means about said different diameters.

3. The solvent delivery pump assembly of claim 2, wherein a cleaning channel/passageway is disposed between said first and second pump heads of each of said two pump units, and is provided so as to automatically clean atmospheric pressure sides of said sealing means provided on each said single shaft.

4. The solvent delivery pump assembly in accordance with claim 3, wherein said cleaning channel/passageway is transverse to said single shaft, and has a small diameter size in each of said pump units.

5. The solvent delivery pump assembly in accordance with claim 4, further including rotatable cam means for operative association with said single shaft to move same back and forth in each of said pump units.

6. The solvent delivery pump assembly in accordance with claim 3, wherein, in each of said pump units a portion of said eluent flows into said cleaning channel/passageway for washing away any eluent leaked about said sealing means and/or accumulated thereabout in the form of crystallized deposits.

7. A The solvent delivery pump assembly in accordance with claim 1, wherein a ratio of the volume of said primary pump to that of said secondary pump is about 2:1.

8. The solvent delivery pump assembly in accordance with claim 1, wherein said primary and secondary pumps are connected in series.

* * * * *